(12) United States Patent
Powers

(10) Patent No.: US 6,230,054 B1
(45) Date of Patent: May 8, 2001

(54) APPARATUS FOR CONTROLLING DELIVERY OF DEFIBRILLATION ENERGY

(75) Inventor: Daniel J Powers, Issaquah, WA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/299,180

(22) Filed: Apr. 23, 1999

(51) Int. Cl.$^7$ ................................................ A61N 1/39
(52) U.S. Cl. ................................................ 607/5
(58) Field of Search ................................ 607/4.5, 63

(56) References Cited

U.S. PATENT DOCUMENTS

| | | |
|---|---|---|
| 4,504,773 | 3/1985 | Suzuki et al. . |
| 4,637,397 | 1/1987 | Jones et al. . |
| 4,745,923 | 5/1988 | Winstrom . |
| 4,850,357 | 7/1989 | Bach, Jr. . |
| 4,953,551 | 9/1990 | Mehra et al. . |
| 4,998,531 | 3/1991 | Bocchi et al. . |
| 5,078,134 | 1/1992 | Heilman et al. . |
| 5,083,562 | 1/1992 | De Coriolis et al. . |
| 5,111,816 | 5/1992 | Pless et al. . |
| 5,222,492 | 6/1993 | Morgan et al. . |
| 5,225,769 | 7/1993 | Fincke et al. . |
| 5,230,336 | 7/1993 | Fain et al. . |
| 5,249,573 | 10/1993 | Fincke et al. . |
| 5,395,394 | 3/1995 | Cameron et al. . |
| 5,443,490 | 8/1995 | Flugstad . |
| 5,472,454 | 12/1995 | Ozawa . |
| 5,594,287 | 1/1997 | Cameron . |
| 6,104,953 | * 8/2000 | Leyde ........................ 607/4 |
| 6,119,039 | * 9/2000 | Leyde ........................ 607/5 |

FOREIGN PATENT DOCUMENTS

| | | |
|---|---|---|
| WO93/16759 | 9/1993 | (WO) . |
| WO94/22530 | 10/1994 | (WO) . |

* cited by examiner

*Primary Examiner*—Jeffrey R. Jastrzab

(57) ABSTRACT

An automatic external defibrillator is described that includes a high voltage delivery circuit for producing an electrical pulse to defibrillate a patient. In a preferred embodiment the electrical pulse is a biphasic or multiphasic electrical pulse. In one embodiment, the delivery circuit includes a high voltage capacitor coupled with a bridge circuit. The capacitor stores electrical energy for delivery to the patient, and the bridge circuit has four switching elements that are selectively switched to steer the current through the patient. A disarm circuit shunts the bridge circuit and operates to route energy away from the bridge circuit in the event a fault condition is detected, such as a short circuit at the patient electrodes. An example disarm circuit is a series-connected SCR and resistor. Also, a limiting circuit element (such as a resistor or an inductor) is provided in series with the capacitor. Together with the disarm circuit, the limiting circuit element reduces the voltage experienced by the bridge circuit switching elements when switched off in response to the detected fault condition. Consequently simpler, more robust, and less expensive high voltage delivery circuits are provided, as compared to conventional defibrillator circuit designs. A snubber circuit is also provided to prevent voltage from reaching the patient when the device is in standby mode.

58 Claims, 3 Drawing Sheets

APPARATUS FOR CONTROLLING DELIVERY OF DEFIBRILLATION ENERGY

BACKGROUND OF THE INVENTION

1. Field of the Invention

This invention relates generally to a method and apparatus for delivering electrical energy produced by a defibrillator to a patient experiencing ventricular fibrillation ("VF"), and more particularly to a method and apparatus for controlling the delivery of electrical energy produced by an external defibrillator. The circuit of this invention allows for active and passive protection of the high energy delivery circuit in the event of a fault condition. The circuit also enables the patient to be protected from high voltage when the device is in standby or monitoring mode. The circuit provides a reliable and safe means of protecting the H-bridge from an over-current condition while increasing patient and operator safety. The circuit also has the advantage of being simple and inexpensive while maintaining a high degree of effectiveness.

2. Description of the Prior Art

Each day thousands of Americans are victims of cardiac emergencies. Cardiac emergencies typically strike without warning, oftentimes striking people with no history of heart disease. The most common cardiac emergency is sudden cardiac arrest ("SCA"). It is estimated that more than 1000 people per day are victims of SCA in the United States alone; this translates into one death every two minutes.

SCA occurs when the heart stops pumping blood. Usually SCA is due to abnormal electrical activity in the heart, resulting in an abnormal rhythm (arrhythmia). One such abnormal rhythm, VF, is caused by abnormal and very chaotic electrical activity in the heart. During VF the heart cannot pump blood effectively. VF may be treated by applying an electric shock to the patient's heart through the use of a defibrillator. The shock clears the heart of the abnormal electrical activity (in a process called "defibrillation") by depolarizing a critical mass of myocardial cells to allow spontaneous organized depolarization to resume, thus restoring normal function. Because blood may no longer be pumping effectively during VF, the chances of surviving decrease with time after the onset of the emergency. Brain damage can occur after the brain is deprived of oxygen for four to six minutes.

External defibrillators send electrical pulses to the patient's heart through electrodes applied to the patient's torso. External defibrillators are typically located and used in hospital emergency rooms, operating rooms, and emergency medical vehicles. Of the wide variety of external defibrillators currently available, automatic and semi-automatic external defibrillators (AEDs) are becoming increasingly popular because they can be used by relatively inexperienced personnel. Such defibrillators can also be especially lightweight, compact, and portable.

AEDs must include circuitry capable of handling the high voltages and high currents associated with electrical defibrillation. In some instances, suitable components with the required electrical characteristics are not readily available, and the AED designer must instead rely on multiple component configurations where, functionally, a single component would suffice.

Additionally, AEDs require monitoring and control circuitry to protect the patient, as well as the AED circuitry itself, in the event of a fault condition. One common fault condition occurs as a result of variations in load impedances, such as those resulting from short circuits or open circuit conditions. The high voltages applied to patients may also create situations, such as arcing between electrodes or arcing between patient wires, that could also lead to failure of the therapy electronics if not properly protected. Such monitor and control circuitry is made increasingly complex by the multiple component configurations included in currently available AEDs.

One method employed by currently available defibrillators to solve this problem is by measuring patient impedance using a low-level signal prior to delivering a shock. The disadvantage of this method is that it relies heavily on the accuracy of the low-level signal measurement relative to the actual impedance (i.e., impedance detected during the high voltage pulse delivered during defibrillation). As will be appreciated by those of skill in the art, the low-level signal cannot predict all behaviors of the external circuit during defibrillation. An example of a condition that cannot be predicted is arcing.

Another method, employed by the ForeRunner® (manufactured by Heartstream, Inc., Seattle, Wash.), is to measure impedance during the initial portion of the waveform and to allow the circuit to continue if impedance is within tolerable limits. Toward that end a 20Ω resistor is placed in series for the first 100 μs that the voltage is delivered. During that time, the resistance across the electrodes is tested to ensure that the connection has not been shorted by monitoring the voltage across a 0.05Ω current sense resistor. Providing a resistance in series during the initial voltage delivery, ensures that the circuit will not be subjected to excessive current in the event that there is a short condition. However, if a fault occurs after the first 100 the circuit could be exposed to excessive currents.

What is needed, therefore, is an AED with a fault protection circuit that is capable of actively protecting the high voltage H-bridge. Protection of the H bridge can be accomplished by switching the bridge off during a fault condition, and/or passively protecting the high voltage bridge, e.g. by allowing the circuit to tolerate the fault condition. Further what is needed is a way to protect the H-bridge from valid load conditions while minimizing the exposure of the patient, or patient simulated load, to the energy stored in the AED. Finally what is needed is a way to protect the operator and/or patient in the event of a discharge to an abnormally high patient load.

SUMMARY OF THE INVENTION

In accordance with the present invention, an apparatus and method is provided for producing and controlling a high energy pulse for application to a patient experiencing VF. A storage circuit stores electrical energy and a steering circuit delivers the electrical energy from the storage circuit to the patient. A protection circuit is coupled with the storage circuit and with the steering circuit. The protection circuit selectively controls the delivery of the electrical energy from the storage circuit to the steering circuit. The protection circuit may include a disarm circuit that selectively shunts the electrical energy way from the steering circuit and patient. The protection circuit may include a limit circuit that limits the rate of delivery of the electrical energy from the storage circuit to the steering circuit. The rate at which electrical energy is delivered is measured and compared to a predetermined range of acceptable rates. If the rate falls within the acceptable range, then electrical energy continues to be delivered. If, however, the rate does not fall within the accepted range, the disarm circuit is enabled and the delivery of the electrical energy to the steering circuit is interrupted. Determination of whether the rate falls within a predetermined acceptable range occurs all the time, thus the disarm circuit can be enabled at any time the rate falls outside the accepted range. The limit circuit and disarm circuit together may limit a maximum voltage applied across the steering circuit when the delivery of electrical energy is interrupted.

This invention provides the advantage of limiting the exposure of the external circuit to high voltage/energy in the event of an over-current load condition. These advantages are achieved with the use of lower cost, readily available components.

DESCRIPTION OF THE PREFERRED EMBODIMENTS

Figure 1:
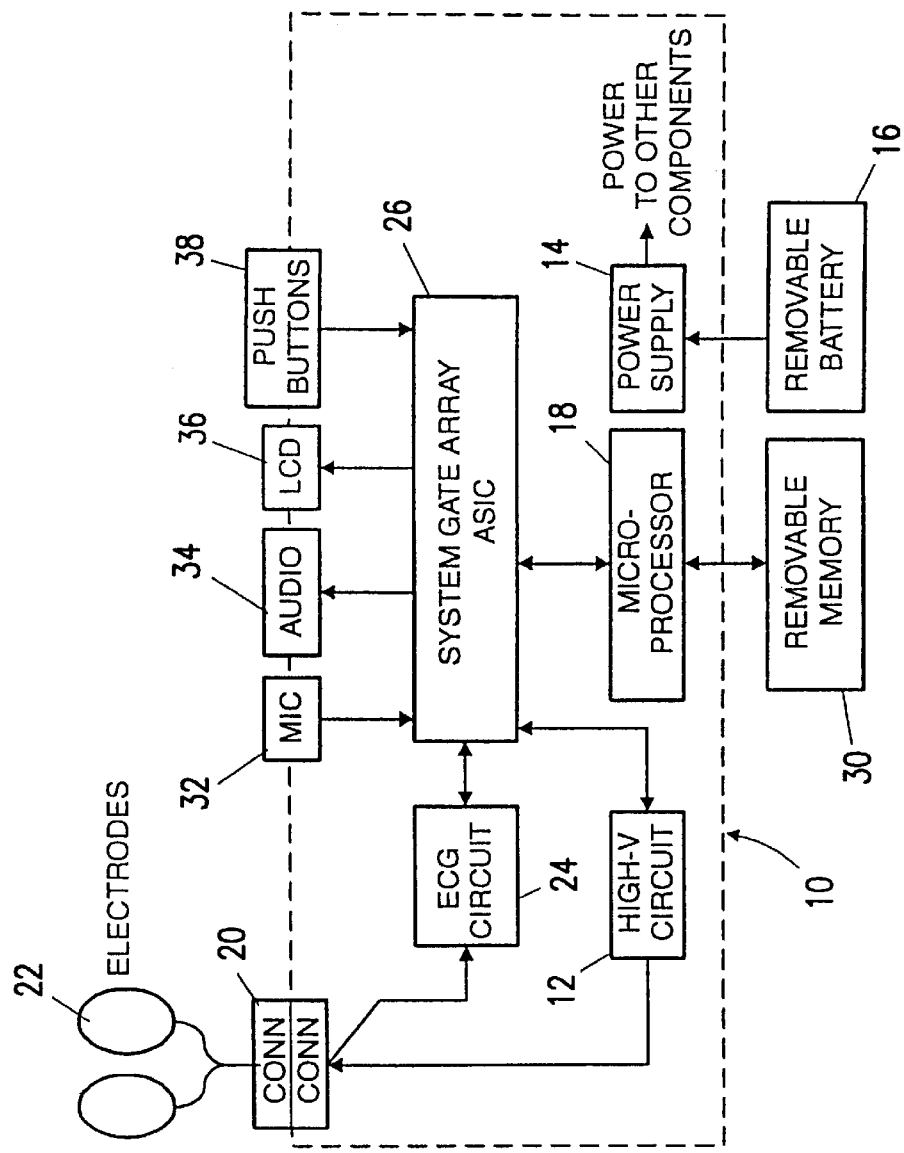
FIG. 1 is a functional block diagram depicting a defibrillator according to an embodiment of the present invention.

Currently available external defibrillators provide either a monophasic or biphasic electrical pulse to a patient through electrodes applied to the chest. Monophasic defibrillators deliver an electrical pulse of current in one direction. Biphasic defibrillators deliver an electrical pulse of current first in one direction and then in the opposite direction. When delivered external to the patient, these electrical pulses are high energy (typically in the range of 30 J to 360 J). This invention may be employed by defibrillators that generate monophasic, biphasic or multiphasic waveforms. Additionally, this invention may be employed by defibrillators that allow the user to select the waveform type.

Defibrillators employing a monophasic waveform are well known in the art. While this invention may be used with a defibrillator employing a monophasic waveform, it is believed that the solution described herein is primarily beneficial for defibrillators that deliver biphasic or multiphasic waveforms.

An example of an AED employing a biphasic waveform is described in U.S. Pat. No. 5,607,454, entitled "Electrotherapy Method and Apparatus," the disclosure of which is incorporated herein by reference. Such defibrillators employ a high voltage bridge circuit for steering the biphasic pulse applied to the patient. The energy delivered to the patient is first stored in an energy storage circuit such as a capacitor, with associated voltages commonly in the range of 1000–2500 V. Prior to delivery of the electrical energy to the patient, one or more of the components of the bridge circuit must withstand this voltage without significant leakage.

Should energy delivery via the bridge circuit be halted due to a fault condition, the corresponding currents and voltages handled by the bridge components are quite high. Given the components currently available to the AED designer, today's bridge circuits commonly include as many as eight to ten distinct switching elements. Correspondingly, the control circuitry associated with switching these elements is relatively complex. The circuit component numbers and complexity required by such AEDs can result in increased expense, potentially lowered reliability, and reduced portability.

In accordance with the present invention, embodiments of an external defibrillator are provided that have a high voltage bridge circuit using only five switching elements to steer the biphasic or multiphasic pulse. In an electrical path separate from the bridge circuit, a sixth switching element is provided for discharging/disarming the energy storage capacitor in the event of a fault. An additional switching element or elements can be provided for current initiation and commutation control. In the following description, certain specific details are set forth in order to provide a thorough understanding of embodiments of the present invention. It will be clear, however, to one skilled in the art, that the present invention can be practiced without these details. In other instances, well-known circuits have not been shown in detail in order to avoid unnecessarily obscuring the description of the various embodiments of the invention. Also not presented in any great detail are those well-known control signals and signal timing protocols associated with the internal operation of defibrillators.

FIG. 1 is a functional block diagram depicting a defibrillator or AED 10 having a high-voltage delivery circuit 12 in accordance with an embodiment of the present invention. The AED 10 includes a power supply 14, which is powered by an energy source such as a removable battery 16 and provides power to other components of the AED. A microcontroller or processor 18 controls the operation of the various components of the AED 10. The high-voltage delivery circuit 12 delivers a pulse of electrical energy to a patient via an electrode connector or interface 20 and electrodes 22.

An electrocardiogram (ECG) circuit 24 acquires and processes the patient's ECG signals through the electrodes 22 and sends the signals to the processor 18 via a system gate array 26. The system gate array 26 is preferably a custom application-specific integrated circuit (ASIC) integrating many of the defibrillator functions (including user interface control and many of the internal functions) and interfacing the processor 18 with other components of the AED 10. Providing the separate system gate array or ASIC 26 allows the processor 18 to focus on other tasks. Of course, the functionality of the ASIC 26 could be included within the operations performed by the processor 18, or could be replaced by discrete logic circuit components or a separately dedicated processor.

The AED 10 also includes a memory device 30. As depicted in FIG. 1, memory device 30 is a removable PCMCIA card or magnetic tape. AED 10 also includes user interface components such as a microphone 32, an audio speaker 34, an LCD display panel 36, and a set of push-button controls 38. Those skilled in the art will understand that a number of other components are included within the AED 10 (e.g., a system monitor and associated status indicators), but are not shown in order to avoid unnecessarily obscuring the description of embodiments of the invention.

Figure 2:
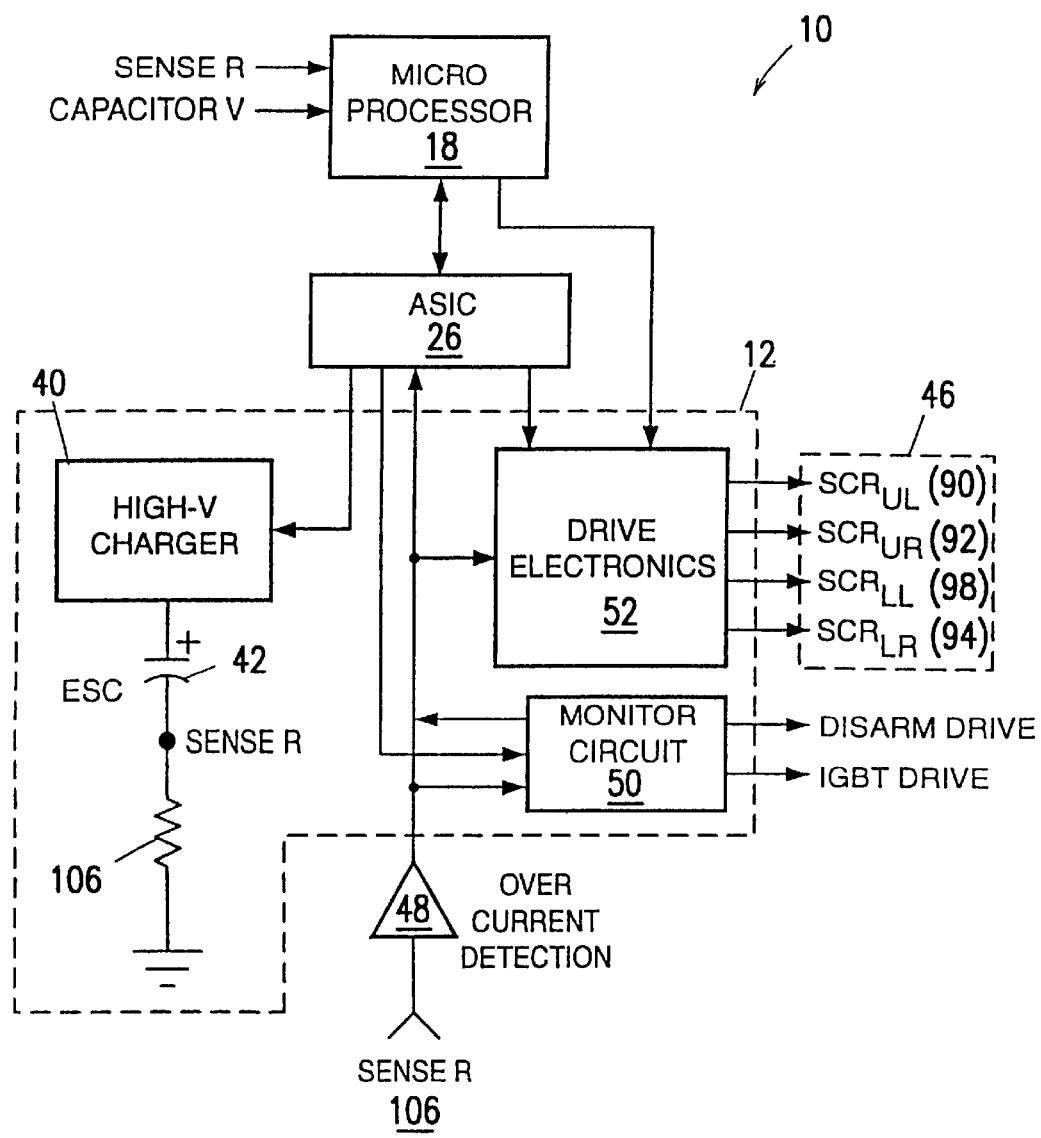
FIG. 2 is a functional block diagram depicting a high-voltage delivery circuit included in the defibrillator of FIG. 1.

As shown in FIG. 2, the high-voltage delivery circuit 12 includes a number of functional circuit blocks which are both monitored and controlled by the ASIC 26. A high-voltage charging circuit 40, such as a flyback power supply, responds to one or more control signals issued by the ASIC 26 and generates electrical energy for provision to a capacitor 42. By controlling the high voltage charger 40, the ASIC can correct an over voltage condition as a result of measuring voltage on the capacitor 60 while it is charging.

The capacitor 42, which could be an energy storage circuit ("ESC"), stores the electrical energy for delivery to the patient. The electrical energy is delivered to an energy transfer or steering circuit 46 (comprising four silicon controlled rectifier switches, $SCR_{UL}$, $SCR_{UR}$, $SCR_{LL}$, and $SCR_{LR}$) through drive electronics 52. The steering circuit 46 in turn delivers the electrical energy to the patient via the connector 20 and electrodes 22 (shown in FIG. 1).

The protection circuit 48 (shown in FIG. 3) functions to limit energy delivery from the ESC 42 to the steering circuit 46 (and hence to the patient) and to discharge or otherwise disarm the ESC 42 in the event of a fault condition. A monitor circuit 50 senses operations of both the protection circuit 48 and the steering circuit 46 and reports the results of such monitoring to the ASIC 26. ASIC 26 provides instructions to the monitor circuit 50 which controls the disarm drive and IGBT drive of the circuit shown in FIG. 3 to prevent an over-current condition on the bridge. The above-described operations of the steering circuit 46 and the protection circuit 48 are controlled by a drive circuit 52 issuing a plurality of drive signals. Operation of the drive circuit 52 is, in turn, controlled by one or more control signals provided by the ASIC 26 and the microprocessor 18.

Figure 3:
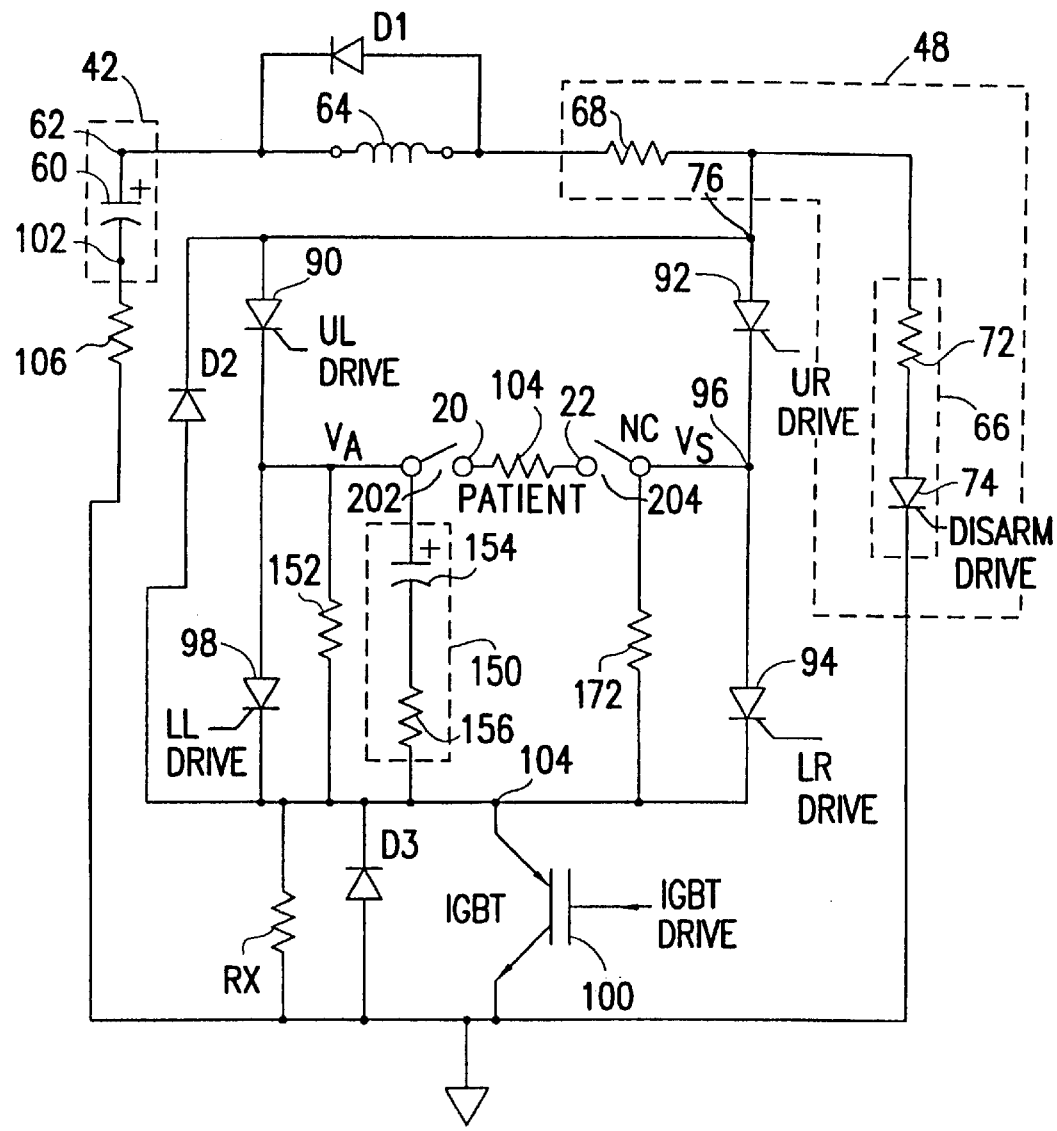
FIG. 3 is a schematic diagram depicting certain details of a first embodiment of the high-voltage delivery circuit of FIG. 2.

FIG. 3 is a more detailed depiction of the invention shown in FIG. 2.

An ESC 42 is provided which is a capacitor (or multiple capacitor unit) 60. Suitable capacitance is approximately 100 μF; the ESC 42 is capable of regularly and reliably storing energy up to approximately 220 J (which corresponds to a voltage of approximately 2100 VDC). The capacitor 60 has a positive terminal or node 62. The energy storage circuit provides energy to a steering circuit 46 which, in turn, controls the delivery of energy to a patient 104. The steering circuit 46 enables the circuit to deliver either a biphasic or multiphasic energy pulse to the patient 104.

The steering circuit 46 is configured as an "H-bridge", with four switching elements. The steering circuit 46 includes an upper-left (UL) switching element, such as $SCR_{UL}$ 90, and an upper-right (UR) switching element, such as $SCR_{UR}$ 92. The anode of each of the SCRs 90, 92 is connected to an upper node 76, and the cathode of each of the SCRs is connected to a respective one of two patient terminals 96 (which, in turn, are coupled with the connector 20 and respective ones of the electrodes 22 of FIG. 1). The control terminal or gate of each of the SCRs 90, 92 receives a respective UL or UR drive signal produced by the drive circuit 52 (shown in FIG. 2) to selectively switch the SCRs on. A patient 104 is represented by a resistor, shown in the electrical location of the patient during defibrillator operations.

The steering circuit 46 also includes a lower-left (LL) switching element, such as $SCR_{LL}$ 98, and a lower-right (LR) switching element, such as a $SCR_{LR}$ 94. The anode of the $SCR_{LL}$ 98 and the anode of the $SCR_{LR}$ 94 are each connected to a respective one of the patient terminals 96. The cathode of the $SCR_{LL}$ 98 and the cathode of $SCR_{LR}$ 94 are each connected to a lower terminal or node 104 of the steering circuit 46. The control terminal or gate of the $SCR_{LL}$ 98 receives an LL drive signal from the drive circuit 52 (shown in FIG. 2) to selectively switch the respective SCR on. The control terminal or gate of $SCR_{LR}$ 94 receives a LR drive signal from the drive circuit 52 to selectively switch the SCR on and off.

A high-voltage diode $D_2$ is connected in parallel to $SCR_{UL}$ 90 and $SCR_{LL}$ 98 at nodes 76 and 104. Diode $D_2$ operates to snub inductance in the patient load when the bridge is turning off the current, for example during the commutation interval.

A sense resistor 106 is connected in series with the steering circuit 46, between lower terminal 104 of the steering circuit 46 and the negative terminal of the energy steering circuit 42 at node 102. A suitable resistance value for the sense resistor 106 is approximately 50 mΩ, and is preferably of the low-value precision resistor type commonly used as an electric shunt in ammeters. In a preferred embodiment, the monitor circuitry 50 (shown in FIG. 2) is an over-current/waveform abort control logic (OIWAL). If an over-current detection is "TRUE," or the switch disarm signal is asserted, the OIWAL performs the necessary steps to shut down the patient load current and safely disarm the ESC 42. Further details of how the drive is disarmed is discussed below.

Additionally, the information from the sense resistor 106 can be provided to the microprocessor 18. The microprocessor can then perform time-integration calculations to obtain information concerning the voltage across the capacitor 60 during defibrillation energy delivery operations.

A limit circuit includes an inductor 64 is connected in series between the positive terminal of the energy storage circuit 42 at node 62 and resistor 68. A suitable value for the inductor 64 is between 100 and 200 μH, preferably 150 μH. A high voltage diode $D_1$ is connected in parallel to the inductor 64 at nodes 62 and 80. The inductor 64 controls the rate at which the current that is delivered to the steering circuit 46 by the ESC 42 can increase. The advantage of providing the inductor 64 in series with the ESC 42 is that by slowing the rate at which the current through the steering circuit 46 can ramp up, additional time is provided for the monitor circuit 50 to instruct a disarm circuit to disconnect the bridge in the event of an over-current situation. Further, the inductor 64 controls dI/dt such that a fixed current threshold can be used for over-current detection. The advantage of providing diode $D_1$ in parallel to the inductor 64 is that the diode functions to snub the inductor during current interruption.

The protection circuit 48 of FIG. 2 is shown in FIG. 3 as two distinct subcircuits—namely, a current limit resistor 68 and a disarm circuit 66.

The current limit resistor 68 is connected in series between inductor 64 (which is connected to the positive terminal 62 of the capacitor 60) and the upper node 76 of the steering circuit 46. The limit resistor 68 limits maximum current flow from the inductor 64 through the steering circuit; a suitable resistance value for the limit resistor 68 is between approximately 3–7Ω, more preferably 5Ω.

The disarm circuit 66 includes a disarm resistor 72 (with a suitable resistance value being between approximately 3–7Ω, more preferably 5Ω) and an SCR 74. The disarm resistor 72 and SCR 74 are connected in series between the upper terminal 76 of the steering circuit 46 and the negative terminal 102 of the capacitor 60, thereby providing an electrical path shunting the steering circuit. If a fault condition is detected (such as an over-current condition), the disarm SCR 74 is switched on and the energy stored in the capacitor 60 substantially dissipated in the disarm resistor 72 and the limit resistor 68. The disarm SCR 74 is selectively switched on by a disarm drive signal provided by the drive circuitry 52 shown in FIG. 2.

Another aspect of the invention is that it provides a mechanism to isolate the patient from the high voltages when the defibrillator is in monitoring mode, thus keeping current from leaking onto the patient 104 prior to delivery of the therapeutic energy pulse. Resistors 152 and 172 function to ground the patient and the ECG circuitry 24, thus preventing current leakage during standby operations. Resistors 152 and 172 are selected to drain the upper SCR leakage currents when the ESC 42 is charging or charged in normal operation. IGBT 100 is left on (during the monitoring mode) to facilitate bleed off of the leakage through resistors 152 and 172. The impedance of resistors 152 and 172 is selected so that under worst case operating conditions a minimal voltage is present at the isolation relay 200 contacts. A suitable value for resistors 152 and 172 is between approximately 5–10Ω, more preferably 9.4 kΩ.

An important aspect of this invention is that leakage resistors 152 and 172 are returned to the collector of IGBT 100. This allows the resistors 152, 172 to have a low resistance value without compromising commutation of the H-bridge. For example, if the resistors were returned to ground, the current flowing through the upper SCRs might exceed the hold current and the SCRs would stay on between phases. If the SCRs stayed on, a cross-conduction of the H-bridge would occur. These resistors also serve as a path to remove charge from a snubber network 150 during the commutation interval.

Additionally resistor $R_x$ and high voltage diode $D_3$ are provided in parallel to IGBT 100 collector-emitter at nodes 104 and 82. Diode $D_3$ prevents a negative voltage across IGBT 100 during high impedance aborts. A high impedance abort occurs, for example, when the patient impedance at 104 is greater than 200Ω. Typically when patient impedance exceeds 200Ω the shock is aborted because it is not possible to complete the therapeutic shock without resulting in an over-voltage condition on the IGBT 100 during the commutation interval.

Resistor $R_x$ bleeds off IGBT collector-emitter capacitance during commutation interval. This results in a reduction or elimination of residual voltage at $V_A$ or $V_S$ prior to initiation of the next phase of the shock. Where $V_A$ is the voltage at the apex of the patient; $V_S$ is the voltage at the sternum of the patient.

The snubber network 150 has a capacitor 154 and a resistor 156. The capacitor 154 and resistor 156 are connected in series. Capacitor 154, resistor 156 and inductor 64 function to limit the rate of change of voltage across the $SCR_{LL}$ 98 when patient impedance is high. By controlling the rate of change of voltage (dV/dT), $SCR_{LL}$ 98 will not accidentally turn on when current is flowing from $SCR_{UL}$ 90 to $SCR_{LR}$ 94 during the first phase of the energy delivery, which might otherwise occur as a result of the voltage change at node 148. Suitable values for capacitor 154 is from 0.007 to 0.03 μF, preferably 0.01 μF; suitable values for resistor 156 is from 25 to 100Ω, preferably 50Ω.

Isolation relay 200, comprising switches 202 and 204, is provided respectively between nodes 20 and 22 and patient 104. The isolation relay 200 is used to prevent leakage, impedances or voltages from interfering with the ECG acquisition function during monitoring and charging activities.

Like resistor 152, resistor 172 is provided on the other side of the H-bridge to isolate the patient 104 and the ECG circuitry 24, thus preventing current leakage during standby operations.

The above-described control signals may be provided by any of a wide variety of suitable drive circuits known to those skilled in the art. For example, the control signals applied to the gates of the bridge $SCR_{UL}$ 90, $SCR_{UR}$ 92, $SCR_{LR}$ 94, $SCR_{LL}$ 98, may each be suitably provided by a corresponding pulse transformer. The secondary coil of each of the transformers may be tied directly to the corresponding SCR gate, with the SCRs designed so that, once triggered and conducting, they will tolerate the short-circuit on the gate-cathode junction that occurs with transformer saturation. Because of the more precise timing requirements for defibrillator disarm operations, the disarm SCR 74 may, for example, be suitably controlled by a logic-level MOSFET switching a bipolar pull-up transistor (not shown). A switching circuit is also provided, shown as IGBT 100. The control signal applied to turn IGBT 100 on and off may, for example, be provided by bipolar pull-up and pull-down transistors (not shown), respectively, which may themselves be triggered by logic-level MOSFET devices (not shown).

The operation of the circuit structure shown in FIG. 3 will now be described. The capacitor 60 is charged by the charging circuitry 40 (shown in FIG. 2) to approximately 2000–2400 V, with the positive terminal 64 having a positive voltage relative to the negative terminal 102. During monitoring operations, the capacitor 60 is fully charged, but no defibrillation energy is delivered to the patient pending completion of ECG monitoring by the ECG circuit 24 (shown in FIG. 1). During standby operation IGBT 100 is on. If the results of the ECG monitoring indicate that defibrillation energy should be delivered to the patient the isolation relay 200 is closed. After an appropriate settling time, $SCR_{UL}$ 90 and $SCR_{LR}$ 94 are turned on and conduction is initiated. During the first phase of the biphasic pulse delivery, current flows from the positive terminal 62 of the capacitor 60 through the inductor 64, limit resistor 68, $SCR_{UL}$ 90, the patient, $SCR_{LR}$ 94, IGBT 100 and the sense resistor 106. When the microprocessor 18 has determined that phase 1 of the waveform is nearing completion, it signals the ASIC 26 to terminate phase 1. Following a brief pause of approximately 400 μs, known as the commutation interval (or interphase delay), IGBT 100 is turned on and the approximately 10 μs later $SCR_{UR}$ 92 and $SCR_{LL}$ 98 are turned on, and electrical energy is further discharged through the patient in the second phase of the biphasic pulse applied to the patient. As will be appreciated by those of skill in the art, delivery of a multiphasic pulse would require these steps to be repeated until the desired number of phases had been achieved. Thus, no specific description of how to deliver a multiphasic pulse is provided.

SCRs of the type suitable for use in the steering circuit 46 and as the disarm SCR 74 are currently readily available. These SCRs can withstand the high voltage and currents occurring during defibrillation operations, and can also survive relatively intense transient effects, such as might occur due to a short circuit or when energy delivery operations are interrupted.

As is well known in the art, one disadvantage of SCRs is that, once turned on, they are not easily turned off absent a forced current commutation. Thus, the energy steering circuit 46 requires at least one switching element that can be turned off for purposes of current commutation and reversing polarity during biphasic energy delivery. Switching elements that can withstand the high voltages and currents that may occur during defibrillation operations are not readily or cost-effectively available. For example, readily available IGBTs can safely withstand a voltage of 1200 V applied across the collector and emitter. In the past IGBTs have been stacked in an effort to overcome limitations on voltage tolerances. However, this solution involves unnecessary complications to the bridge design. Those skilled in the art will appreciate that, if the above-described IGBT 100 were itself to "open" the steering circuit 46 to interrupt delivery of electrical energy from the capacitor 60 (when fully or near-fully charged), the voltage experienced by the IGBT 100 would significantly exceed the rated 1200 V limit thereby damaging the circuit.

In accordance with the embodiment of the invention depicted in FIG. 3, the IGBT 100 is protected from elevated voltages and currents. In the event of an over-current condition (caused, for example, by a short-circuit at the patient electrodes 22), the disarm SCR 74 is first switched on to begin discharging the capacitor 60 through the limit resistor 68 and the disarm resistor 72. Because the resistors 68 and 72 form a voltage divider, the IGBT 100 can then be shut off at a lower collector-to-emitter voltage than would otherwise be the case. Thus, a single IGBT 100 may be employed, rather than the conventional multiple component approach found in current AED designs. Further, because the disarm circuit is external to the H-bridge, the ESC 42 can be safely disarmed without exposing the patient 104 to high voltages. In the event of a high impedance load fault, the microprocessor 18 can signal the OIWAL to protect the H-bridge and the patient load in a similar fashion. As will be appreciated by those of skill in the art a high impedance load fault can occur at several times during operation of the bridge. Initially, a high impedance load fault can occur during the initial voltage delivery (for example where the electrode pads are shorted out). Additionally, a high impedance load fault can occur at the end of phase one, where, for example, more than 1200 V remains on the capacitor. In either situation, the microprocessor signals the OIWAL to protect the patient and the H-bridge by aborting the shock. However, where the load fault is detected at the end of a phase, the result is that the shock delivered comprises only the phases delivered. Specifically, where the fault occurs at the end of phase one, the result is that a monophasic shock to the patient.

The embodiment of the present invention shown in FIG. 3 provides a relatively inexpensive and robust defibrillation energy delivery circuit. In contrast with currently available designs, the provision of the disarm circuit 66 allows a bridge circuit design comprised of four individual switching elements, which are readily available and low cost SCRs. In the event of a fault condition, such as an over-voltage condition, the energy stored in the capacitor 60 can be similarly discharged safely through the disarm circuit 48.

In operation, the disarm circuit 66 is triggered in response to an over-current condition. Approximately 1 $\mu$s later, the IBGT 100 is turned off by OIWAL. In a preferred embodiment, the over-current trip point is set at approximately 80 Amps. At the maximum voltage of the capacitor the dI/dt of the inductor is approximately 14 A/$\mu$s. When the SCR is fired the resistors form a dividing network (with a ratio of approximately 2:1), where the top of the H-bridge is at the center point. When the IGBT 100 is turned off, the maximum voltage at the collector is $V_{CAP}/2$. More importantly, as the IGBT 100 is turning off there is effectively a 5$\Omega$ snubber resitance across the collector-emitter junction. This provides a high degree of margin for RBSOA, which is the safe operating area of the IGBT 100 during turn-off.

Those skilled in the art will understand that certain of the circuits and components shown in FIGS. 1–3 have not been described in particular detail. In such case, the circuits and components are the type whose function and interconnection is well known in the art, and one skilled in the art would be able to use such circuits and components in the described combination to practice the present invention. The internal details of these particular circuits are not critical to the invention, and a detailed description of such internal circuit operation is therefore not required.

It will be appreciated that, while specific embodiments of the invention have been described herein for purposes of illustration, various modifications may be made without deviating from the spirit and scope of the invention. Those skilled in the art will appreciate that many of the advantages associated with the circuits described above in connection with FIG. 3 may be provided by other circuit configurations. Those skilled in the art will also understand that a number of suitable circuit components, other than those particular ones described above, can be adapted and combined in a variety of circuit topologies to implement a high voltage delivery circuit in accordance with the present invention. Accordingly, the invention is not limited by the disclosed embodiments, but instead the scope of the invention is determined by the following claims.

What is claimed:

1. A circuit for producing a high energy pulse for application to a patient experiencing ventricular fibrillation, comprising:
   a storage circuit operable to store electrical energy;
   a steering circuit coupled with the storage circuit, the steering circuit being adapted for coupling with the patient and operable to deliver the electrical energy from the storage circuit to the patient; and
   a protection circuit coupled with the storage circuit and with the steering circuit and operable to respond to a detected fault condition to selectively control the delivery of electrical energy from the storage circuit to the steering circuit.

2. A circuit according to claim 1 wherein the protection circuit includes a disarm circuit operable to selectively shunt delivery of the electrical energy away from the steering circuit.

3. A circuit according to claim 2 wherein the disarm circuit includes a switching element and a resistive element, the switching element selectively electrically connecting the storage circuit with the resistive element to dissipate the electrical energy therein.

4. A circuit according to claim 3 wherein the switching element is a silicon-controlled rectifier.

5. A circuit according to claim 1 wherein the protection circuit includes a limit circuit coupled between the storage circuit and the steering circuit and operable to limit the rate of current increase from the storage circuit to the steering circuit.

6. A circuit according to claim 5 wherein the limit circuit includes a resistive element operable to limit current flow from the storage circuit to the steering circuit.

7. A circuit according to claim 1 wherein the protection circuit includes a limit circuit coupled between the storage circuit and the steering circuit and operable to limit the time rate of change of delivery of the electrical energy from the storage circuit to the steering circuit.

8. A circuit according to claim 7 wherein the limit circuit includes an inductive element coupling the storage circuit with the steering circuit, the inductive element operable to limit the time rate of change of current flow from the storage circuit to the steering circuit.

9. A circuit according to claim 1 wherein the protection circuit includes a disarm circuit and a protection circuit, the disarm circuit being operable to selectively shunt delivery of the electrical energy away from the steering circuit, and the limit circuit being operable to limit delivery of the electrical energy from the storage circuit to the steering circuit, the disarm circuit and limit circuit together operable to substantially limit a maximum voltage applied across the steering circuit.

10. A circuit according to claim 1 wherein the storage circuit includes a capacitor having first and second terminals and operable to store the electrical energy therebetween, wherein the steering circuit includes a bridge circuit coupled with the first and second terminals of the capacitor and operable to deliver a biphasic pulse of the electrical energy to the patient, wherein the protection circuit includes a series-connected switching element and a first resistive element shunting the bridge circuit, and wherein the protection circuit includes a second resistive element coupling the first terminal of the capacitor with the bridge circuit, the switching element operable to electrically connect the first and second terminals together through the first and second resistive elements to substantially dissipate the electrical energy therein, the first and second resistive elements forming a voltage divider to limit a maximum voltage applied across the bridge circuit.

11. A circuit according to claim 1 wherein the storage circuit includes a capacitor having first and second terminals and operable to store the electrical energy therebetween, wherein the steering circuit includes a bridge circuit coupled with the first and second terminals of the capacitor and operable to deliver a biphasic pulse of the electrical energy to the patient, wherein the protection circuit includes a series-connected switching element and a resistive element shunting the bridge circuit, and wherein the protection circuit includes an inductive element coupling the first terminal of the capacitor with the bridge circuit, the switching element operable to electrically connect the first and second terminals together through the resistive and inductive elements to substantially dissipate the electrical energy in the resistive element, the inductive and resistive element together limiting a maximum voltage applied across the bridge circuit.

12. A circuit for producing a high energy pulse for application to a patient experiencing ventricular fibrillation, comprising:
   a storage circuit operable to store electrical energy;
   a steering circuit coupled with the storage circuit, the steering circuit adapted for coupling with the patient and operable to deliver the electrical energy from the storage circuit to the patient; and
   a disarm circuit coupled with the storage circuit and with the steering circuit, the disarm circuit operable to selectively shunt delivery of the electrical energy away from the steering circuit.

13. A circuit according to claim 12 wherein the disarm circuit includes a switching element and a resistive element, the switching element selectively electrically connecting the storage circuit with the resistive element to dissipate the electrical energy therein.

14. A circuit according to claim 13 wherein the switching element is a silicon-controlled rectifier.

15. A circuit according to claim 12 wherein the storage circuit includes a capacitor having first and second terminals and operable to store the electrical energy therebetween, wherein the steering circuit includes a bridge circuit coupled with the first and second terminals of the capacitor and operable to deliver a biphasic pulse of the electrical energy to the patient, and wherein the disarm circuit includes a series-connected switching element and resistive element coupled with the first and second terminals, the switching element operable to electrically connect the first and second terminals together through the resistive element to dissipate the electrical energy therein.

16. A circuit for producing a high energy pulse for application to a patient experiencing ventricular fibrillation, comprising:
   a storage circuit operable to store electrical energy;
   a steering circuit coupled with the storage circuit, the steering circuit adapted for coupling with the patient and operable to deliver the electrical energy from the storage circuit to the patient; and
   a limit circuit coupling the storage circuit with the steering circuit, the limit circuit operable to limit the delivery of the electrical energy from the storage circuit to the steering circuit.

17. A circuit according to claim 16 wherein the limit circuit includes a resistive element operable to limit current flow from the storage circuit to the steering circuit.

18. A circuit according to claim 16 wherein the limit circuit includes an inductive element operable to limit the time rate of change of current flow from the storage circuit to the steering circuit.

19. A circuit according to claim 16 wherein the storage circuit includes a capacitor having first and second terminals and operable to store the electrical energy therebetween, wherein the steering circuit includes a bridge circuit coupled with the first and second terminals of the capacitor and operable to deliver a biphasic pulse of the electrical energy to the patient, and wherein the limit circuit couples the first terminal of the capacitor with the bridge circuit and includes one of a resistive element and an inductive element respectively operable to limit the current flow and the time rate of change of the current flow from the capacitor to the bridge circuit.

20. A circuit for producing a high energy pulse for application to a patient experiencing ventricular fibrillation, comprising:
   a storage circuit operable to store electrical energy;
   a steering circuit coupled with the storage circuit, the steering circuit being adapted for coupling with the patient and operable to deliver the electrical energy from the storage circuit to the patient;
   a disarm circuit coupled with the storage circuit and with the steering circuit and operable to selectively shunt delivery of the electrical energy away from the steering circuit; and
   a limit circuit coupling the storage circuit with the steering circuit and operable to limit delivery of the electrical energy from the storage circuit to the steering circuit, the disarm circuit and limit circuit together operable to substantially limit a maximum voltage applied across the steering circuit.

21. A circuit according to claim 20 wherein the disarm circuit includes a series-connected switching element and a first resistive element, and wherein the limit circuit includes a second resistive element, the switching element operable to electrically connect the storage circuit to the first and second resistive elements to substantially dissipate the electrical energy therein, the first and second resistive elements forming a voltage divider to substantially limit the maximum voltage applied across the steering circuit.

22. A circuit according to claim 20 wherein the disarm circuit includes a series-connected switching element and a resistive element, and wherein the limit circuit includes an inductive element, the switching element operable to electrically connect the storage circuit to the resistive and inductive elements to substantially dissipate the electrical energy in the resistive element, the inductive and resistive element together limiting the maximum voltage applied across the bridge circuit.

23. A circuit according to claim 20 wherein the storage circuit includes a capacitor having first and second terminals and operable to store the electrical energy therebetween, wherein the steering circuit includes a bridge circuit coupled with the first and second terminals of the capacitor and operable to deliver a biphasic pulse of the electrical energy to the patient, wherein the protection circuit includes a series-connected switching element and a first resistive element shunting the bridge circuit, and wherein the protection circuit includes a second resistive element coupling the first terminal of the capacitor with the bridge circuit, the switching element operable to electrically connect the first and second terminals together through the first and second resistive elements to substantially dissipate the electrical energy therein, the first and second resistive elements forming a voltage divider to limit a maximum voltage applied across the bridge circuit.

24. A circuit according to claim 20 wherein the storage circuit includes a capacitor having first and second terminals and operable to store the electrical energy therebetween, wherein the steering circuit includes a bridge circuit coupled with the first and second terminals of the capacitor and operable to deliver a biphasic pulse of the electrical energy to the patient, wherein the protection circuit includes a series-connected switching element and a resistive element shunting the bridge circuit, and wherein the protection circuit includes an inductive element coupling the first terminal of the capacitor with the bridge circuit, the switching element operable to electrically connect the first and second terminals together through the resistive and inductive elements to substantially dissipate the electrical energy in the resistive element, the inductive and resistive element together limiting a maximum voltage applied across the bridge circuit.

25. A circuit for producing a high energy pulse for application to a patient experiencing ventricular fibrillation, comprising:
   a storage circuit having first and second terminals and operable to store electrical energy therebetween;
   a steering circuit coupled with the first terminal of the storage circuit, the steering circuit adapted for coupling with the patient and operable to deliver the electrical energy from the storage circuit to the patient;
   a disarm circuit coupled with the first and second terminals of the storage circuit, the disarm circuit operable to selectively shunt delivery of the electrical energy away from the steering circuit; and
   a switching circuit coupled with the steering circuit and with the second terminal of the storage circuit, the switching circuit operable to electrically connect and disconnect the steering circuit to and from the second terminal of the storage circuit to initiate and interrupt the delivery of electrical energy through the steering circuit, all respectively.

26. A circuit according to claim 25 wherein the switching circuit includes an electrically controlled switch having a node coupled with the steering circuit and with the disarm circuit, and wherein the disarm circuit is operable to provide a clamping voltage level to which the node is substantially clamped, thereby substantially limiting a maximum voltage applied across the switch.

27. A circuit according to claim 26 wherein the switch is an insulated gate bipolar transistor.

28. A circuit according to claim 26 wherein the node is a first node, and wherein the disarm circuit includes first and second series-connected resistors with a second node therebetween coupled with the first node and providing the clamping voltage level.

29. A circuit according to claim 25, further comprising a limit circuit coupling the first terminal of the storage circuit with the steering circuit, the limit circuit operable to limit the rate of delivery of the electrical energy from the storage circuit to the steering circuit.

30. A circuit according to claim 25, further comprising a voltage limiting circuit coupled with the switching circuit, the voltage limiting circuit operable to limit the voltage applied across the switching circuit to no more than a maximum voltage level.

31. In an electrical defibrillator for defibrillating a patient experiencing ventricular fibrillation, a method of delivering electrical energy to the patient, comprising the steps of:
   storing electrical energy;
   initiating delivery of the electrical energy to the patient;
   measuring an electrical value associated with the delivery; and
   if the measured electrical value falls within a predetermined range of acceptable values, then continuing delivery of the electrical energy to the patient; or
   if the measured electrical value does not fall within the range of acceptable values, the method then further comprising the steps of,
      interrupting delivery of the electrical energy to the patient; and
      discharging remaining stored electrical energy.

32. A method according to claim 31 wherein the step of measuring an electrical value includes the step of measuring a current value.

33. A method according to claim 31 wherein the step of measuring an electrical value includes the step of measuring a voltage value.

34. A method according to claim 31 wherein the step of interrupting delivery of the electrical energy to the patient includes the step of forming an electrical path shunting the patient, and wherein the step of discharging remaining stored electrical energy includes the step of substantially dissipating the remaining stored energy in the electrical path.

35. In an electrical defibrillator for defibrillating a patient experiencing ventricular fibrillation, a method of delivering electrical energy to the patient, comprising the steps of:
   storing electrical energy;
   initiating delivery of the electrical energy to the patient;
   limiting the delivery of the electrical energy;
   measuring an electrical value associated with the delivery; and
   if the measured electrical value falls within a predetermined range of acceptable values, then continuing delivery of the electrical energy to the patient; or
   if the measured electrical value does not fall within the range of acceptable values, the method then further comprising the steps of,
      interrupting delivery of the electrical energy to the patient; and
      discharging remaining stored electrical energy.

36. A method according to claim 35 wherein the step of limiting the delivery of the electrical energy includes the step of limiting electrical current.

37. A method according to claim 35 wherein the step of limiting the delivery of the electrical energy includes the step of limiting the time rate of change of electrical current.

38. A method according to claim 35 wherein the step of measuring an electrical value includes the step of measuring a current value.

39. A method according to claim 35 wherein the step of interrupting delivery of the electrical energy to the patient includes the step of forming an electrical path shunting the patient, and wherein the step of discharging remaining stored electrical energy includes the step of substantially dissipating the remaining stored energy in the electrical path.

40. In an electrical defibrillator having a storage circuit coupled with a steering circuit, the storage circuit for storing electrical energy and the steering circuit for directing the electrical energy to a patient, a method of delivering electrical energy to a patient, comprising the steps of:

charging the storage circuit to store electrical energy therein;

forming a first electrical path from the storage circuit to the patient through the steering circuit;

initiating delivery of the electrical energy via the first electrical path;

sensing the rate at which the electrical energy is delivered via the first path; and if the rate falls within a predetermined acceptable range, then continuing to deliver the electrical energy via the first electrical path; or if the rate does not fall within the acceptable range, the method then further comprising the steps of, forming a second electrical path from the storage circuit; and opening the first electrical path.

41. A method according to claim 40 wherein the step of sensing the rate at which the electrical energy is delivered includes the step of sensing a current flow through the first electrical path.

42. A method according to claim 40 wherein the step of forming the second electrical path includes the step of forming an electrical path shunting the first electrical path.

43. A method according to claim 40 wherein if the rate does not fall within the acceptable range, the method further comprising the step of substantially dissipating the electrical energy in the second electrical path.

44. In an electrical defibrillator having a storage circuit coupled with a steering circuit, the storage circuit for storing electrical energy and the steering circuit for directing the electrical energy to a patient, a method of delivering electrical energy to a patient, comprising the steps of:

charging the storage circuit to store electrical energy therein;

forming a first electrical path from the storage circuit to the patient through the steering circuit;

initiating delivery of the electrical energy via the first electrical path;

limiting the delivery of the electrical energy;

sensing the rate at which the electrical energy is delivered via the first path; and if the rate falls within a predetermined acceptable range, then continuing to deliver the electrical energy via the first electrical path; or if the rate does not fall within the acceptable range, the method then further comprising the steps of, forming a second electrical path from the storage circuit; and opening the first electrical path.

45. A method according to claim 44 wherein the step of limiting the delivery of the electrical energy includes the step of limiting electrical current.

46. A method according to claim 44 wherein the step of limiting the delivery of the electrical energy includes the step of limiting the time rate of change of electrical current.

47. A method according to claim 44 wherein the step of sensing the rate at which the electrical energy is delivered includes the step of sensing a current flow through the first electrical path.

48. A method according to claim 44 wherein the step of forming the second electrical path includes the step of forming an electrical path shunting the first electrical path.

49. A method according to claim 44 wherein if the rate does not fall within the acceptable range, the method further comprising the step of substantially dissipating the electrical energy in the second electrical path.

50. In an electrical defibrillator having a storage circuit coupled with a steering circuit, the storage circuit for storing electrical energy and the steering circuit for directing the electrical energy to a patient, a method of delivering electrical energy to a patient, comprising the steps of:

storing electrical energy in the storage circuit;

initiating electrical current flow through the steering circuit; and measuring a current magnitude of the electrical current flow through the steering circuit;

if the current magnitude falls within a predetermined acceptable range, then continuing to allow the electrical current flow through the steering circuit; or if the current magnitude does not fall within the acceptable range, the method then further comprising the steps of, forming an electrical path shunting the steering circuit;

controlling voltage applied across the steering circuit; and stopping the electrical current flow through the steering circuit.

51. A method according to claim 50 wherein the step of controlling voltage applied across the steering circuit includes the step of limiting a maximum voltage applied across the steering circuit.

52. A method according to claim 50 wherein the step of controlling voltage applied across the steering circuit includes the step of limiting the time rate of change of the voltage applied across the steering circuit.

53. A method according to claim 50 wherein if the current magnitude does not fall within the acceptable range, the method further comprising the step of substantially dissipating remaining electrical energy stored in the storage circuit.

54. In an electrical defibrillator having a switching circuit coupling a storage circuit with a steering circuit, the storage circuit for storing electrical energy, the steering circuit for directing the electrical energy to a patient, and the switching circuit for initiating and stopping the transfer of electrical energy from the storage circuit to the steering circuit, a method of delivering electrical energy to a patient, comprising the steps of:

storing electrical energy in the storage circuit;

initiating electrical current flow through the steering circuit; and measuring a current magnitude of the electrical current flow through the steering circuit;

if the current magnitude falls within a predetermined acceptable range, then continuing to allow the electrical current flow through the steering circuit; or if the current magnitude does not fall within the acceptable range, the method then further comprising the steps of, forming an electrical path shunting the steering circuit;

controlling voltage applied across the switching circuit; and stopping the electrical current flow through the steering circuit.

55. A method according to claim 54 wherein the step of controlling voltage applied across the switching circuit includes the step of limiting a maximum voltage applied across the switching circuit.

56. A method according to claim 54 wherein the step of controlling voltage applied across the switching circuit includes the step of limiting the time rate of change of the voltage applied across the switching circuit.

57. A method according to claim 54 wherein the step of controlling voltage applied across the switching circuit includes the steps of:

producing a clamping voltage level in the electrical path shunting the steering circuit; and coupling the switching circuit to the clamping voltage level.

58. A method according to claim 54 wherein if the current magnitude does not fall within the acceptable range, the method further comprising the step of substantially dissipating remaining electrical energy stored in the storage circuit.

* * * * *